United States Patent
Na et al.

(10) Patent No.: US 9,217,165 B2
(45) Date of Patent: Dec. 22, 2015

(54) MUTANT STRAIN OF LACTIC ACID PRODUCING YEAST AND PROCESS FOR PRODUCING LACTIC ACID

(75) Inventors: Kyungsu Na, Kamakura (JP); Kazumi Suda, Kamakura (JP)

(73) Assignee: Toray Industries, Inc. (JP)

( * ) Notice: Subject to any disclaimer, the term of this patent is extended or adjusted under 35 U.S.C. 154(b) by 90 days.

(21) Appl. No.: 14/114,001

(22) PCT Filed: Apr. 27, 2012

(86) PCT No.: PCT/JP2012/061320
§ 371 (c)(1),
(2), (4) Date: Oct. 25, 2013

(87) PCT Pub. No.: WO2012/147903
PCT Pub. Date: Nov. 1, 2012

(65) Prior Publication Data
US 2014/0051138 A1    Feb. 20, 2014

(30) Foreign Application Priority Data

Apr. 28, 2011  (JP) ................... 2011-101578
Jan. 30, 2012  (JP) ................... 2012-016544

(51) Int. Cl.
*C12N 15/81*  (2006.01)
*C12N 9/88*   (2006.01)
*C12N 9/02*   (2006.01)
*C12P 7/56*   (2006.01)
*C12N 9/04*   (2006.01)

(52) U.S. Cl.
CPC .................. *C12P 7/56* (2013.01); *C12N 9/0006* (2013.01); *C12N 15/81* (2013.01)

(58) Field of Classification Search
USPC ........................................ 435/252.3
See application file for complete search history.

(56) References Cited

FOREIGN PATENT DOCUMENTS

| | | |
|---|---|---|
| JP | 2001-516584 A | 10/2001 |
| JP | 2006-521113 A | 9/2006 |
| JP | 2008-029329 A | 2/2008 |
| JP | 2009-517045 A | 4/2009 |
| JP | 2009-142210 A | 7/2009 |
| JP | 2009-171879 A | 8/2009 |
| JP | 2010-115112 A | 5/2010 |
| WO | 2007/097260 A1 | 8/2007 |
| WO | 2009/004922 A1 | 1/2009 |
| WO | 2009/099044 A1 | 8/2009 |
| WO | 2010/001862 A1 | 1/2010 |
| WO | 2010/140602 A1 | 12/2010 |

OTHER PUBLICATIONS

S. Tsuji et al., "Evolutionary relationships of lactate dehydrogenases (LDHs) from mammals, birds, an amphibian, fish, barley, and bacteria: LDH cDNA sequences from Xenopus, pig, and rat," Proc. Natl. Acad. Sci. USA, vol. 91, No. 20, Sep. 27, 1994, pp. 9392-9396 (Abstract only).
A. Adachi et al., "Modification of metabolic pathways of *Saccharomyces cerevisiae* by the expression of lactate dehydrogenase and deletion of pyruvate decarboxylase genes for the lactic acid fermentation at low pH value," J. Ferment. Bioeng., vol. 86, No. 3, 1998, pp. 284-289 (Abstract only).
Sugita, H. et al., "Lactate Dehydrogenase of the Horseshoe Crabs and Their Hybrids," *Zoological Science*, 1984, vol. 1, pp. 421-426.

*Primary Examiner* — Maryam Monshipouri
(74) *Attorney, Agent, or Firm* — DLA Piper LLP (US)

(57) ABSTRACT

A lactic acid-producing yeast mutant which is a mutant of a yeast prepared by introduction of a lactate dehydrogenase gene that results in lactic acid-producing ability, the mutant having, in a medium at pH 3, a lactic acid-producing ability equivalent to or higher than the lactic acid-producing ability of a parent strain of the mutant at a lactic acid fermentation optimum pH.

7 Claims, 3 Drawing Sheets

MUTANT STRAIN OF LACTIC ACID PRODUCING YEAST AND PROCESS FOR PRODUCING LACTIC ACID

TECHNICAL FIELD

This disclosure relates to a lactic acid-producing yeast that can be preferably used in production of lactic acid, and a method of producing lactic acid using the yeast strain.

BACKGROUND

As the problem of emission of carbon dioxide into the atmosphere and the energy problem became obvious, polylactic acid, which is a biodegradable polymer, has been drawing attention in view of its sustainability and as a life cycle assessment (LCA)-oriented product. At present, polylactic acid is mainly produced as L-lactic acid polymers, and highly optically pure L-lactic acid is now being mass produced as the raw material for the polymers.

Further, as polylactic acids having high heat resistance, stereocomplex polylactic acids (Sc-PLAs) are drawing attention. Since Sc-PLAs require as raw materials not only L-lactic acid but also D-lactic acid, which is the optical isomer of L-lactic acid, methods of producing highly optically pure D-lactic acid are now being developed.

Since, as mentioned above, high optical purity is required for lactic acid as a raw material for the polymers, the method of producing the lactic acid is currently limited to lactic acid fermentation by microorganism culture. However, in such a case, the microorganism needs to be cultured while the pH optimum for production of lactic acid by the microorganism (hereinafter referred to as the lactic acid fermentation optimum pH) is maintained. For example, in cases where a lactic acid-producing yeast having a lactic acid fermentation optimum pH of about 4.5 is cultured to produce lactic acid, the pH of the culture liquid needs to be kept at the lactic acid fermentation optimum pH by alkali neutralization to maintain the lactic acid productivity of the lactic acid-producing yeast (see JP 2009-171879 A). If the culture liquid of the lactic acid-producing yeast is neutralized with an alkaline substance for this purpose, by-products such as gypsum may be produced in the subsequent step of separation/purification of lactic acid, depending on the amount of alkaline substance added. This makes the step of separation/purification of lactic acid laborious, resulting in high cost of production of lactic acid. Further, although there was a case where a low-pH-resistant lactic acid-producing yeast was used to produce lactic acid at pH 3, which is a pH lower than the lactic acid fermentation optimum pH of the lactic acid-producing yeast, the lactic acid productivity obtained at a pH lower than the lactic acid fermentation optimum pH is lower than the lactic acid productivity obtained at the lactic acid fermentation optimum pH, which is problematic (see Japanese Translated PCT Patent Application Laid-open No. 2009-517045).

It could therefore be helpful to provide a lactic acid-producing yeast mutant which is resistant to the low-pH state of the culture liquid caused during lactic acid production by culture of a lactic acid-producing yeast, which lactic acid-producing yeast mutant has, in a low-pH state, a lactic acid-producing ability equivalent to or higher than the lactic acid-producing ability at the lactic acid fermentation optimum pH, and a method of producing lactic acid using the mutant.

SUMMARY

We discovered mutations to a lactic acid-producing yeast. We thus provide (1) to (8) below:

(1) A lactic acid-producing yeast mutant which is a mutant of a yeast prepared by introduction of a lactate dehydrogenase gene to give lactic acid-producing ability, the mutant having, in a medium at pH 3, a lactic acid-producing ability equivalent to or higher than the lactic acid-producing ability of the parent strain of the mutant at the optimum pH for lactic acid fermentation.

(2) The lactic acid-producing yeast mutant according to (1), wherein the lactate dehydrogenase gene is a gene encoding D-lactate dehydrogenase or a gene encoding L-lactate dehydrogenase.

(3) The lactic acid-producing yeast mutant according to (1) or (2), wherein the lactate dehydrogenase gene is a gene encoding D-lactate dehydrogenase derived from *Limulus polyphemus*.

(4) The lactic acid-producing yeast mutant according to (1) or (2), wherein the lactate dehydrogenase gene is a gene encoding L-lactate dehydrogenase derived from *Xenopus laevis*.

(5) The lactic acid-producing yeast mutant according to any one of (1) to (4), wherein the yeast belongs to the genus *Saccharomyces*.

(6) The lactic acid-producing yeast mutant according to any one of (1) to (5), wherein the yeast is *Saccharomyces cerevisiae*.

(7) The lactic acid-producing yeast mutant according to any one of (1) to (6), which is a yeast deposited under accession No. NITE BP-1087, NITE BP-1088, NITE BP-1089, NITE BP-1189 or NITE BP-1190.

(8) A method of producing lactic acid, the method comprising culturing the lactic acid-producing yeast mutant according to any one of (1) to (7).

(9) The method of producing lactic acid according to (8), comprising maintaining the culture liquid of the lactic acid-producing yeast mutant at a pH of not more than 3.

(10) The method of producing lactic acid according to (8), comprising culturing the lactic acid-producing yeast mutant without alkali neutralization of the culture liquid.

The lactic acid-producing ability of a lactic acid-producing yeast can be maintained even in a low-pH state caused by lactic acid so that the lactic acid production process can be simplified and the cost of lactic acid production can be reduced.

DETAILED DESCRIPTION

The lactic acid-producing yeast mutant means a mutant obtained by mutation treatment of a yeast prepared by introducing a lactate dehydrogenase gene that results in a lactic acid-producing ability. The lactic acid-producing yeast mutant is described below in more detail.

Examples of the yeast include yeasts belonging to the genus *Saccharomyces*, genus *Kluyveromyces*, genus *Schizosaccharomyces*, genus *Toluropusis*, genus *Candida*, genus *Pichia*, genus *Yarrowia*, genus *Hansenula*, genus *Issachenkia*, genus *Trichosporon* and genus *Yamadazyma*. Specific examples of the yeast include *Saccharomyces cerevisiae, Saccharomyces copsis, Saccharomyces sonorensis, Saccharomyces uvarum, Candida sonorensis, Candida glabrata, Candida lipolytica, Candida methanesorbosa, Candida ethanolica, Candida krusei, Pichia kudriavzevii, Pichia galeiformis, Pichia deserticola, Pichia membranifaciens, Pichia fermentans, Toluropusis glabrata, Torulaspora pretoriensis, Kluyveromyces lactis, Kluyveromyces marxianus, Kluyveromyces thermotolerans, Schizosaccharomyces pombe, Schizosaccharomyces bulderi, Issachenkia orientalis, Hansenula polymorphs* and *Yamadazyma styptic*. The yeast preferably is a yeast belonging to the genus *Saccharomyces*. The yeast is more preferably *Saccharomyces cerevisiae*.

Since most yeasts do not originally express lactate dehydrogenase at high enzyme activity, they cannot highly produce lactic acid. Therefore, to obtain a lactic acid-producing yeast, it is necessary to give lactate dehydrogenase activity to a yeast by introducing a lactate dehydrogenase gene thereto. Methods of giving lactate dehydrogenase activity to a yeast by introducing a lactate dehydrogenase gene thereto are known. Examples of the methods include the methods disclosed in WO 2010/140602 and WO 2009/099044.

The lactate dehydrogenase gene to be introduced to a yeast is not limited as long as the gene encodes a protein having a lactate dehydrogenase activity, that is, an activity to convert reduced nicotinamide adenine dinucleotide (NADH) and pyruvic acid to oxidized nicotinamide adenine dinucleotide (NAD+) and lactic acid. In cases where L-lactic acid is to be produced, it is preferred to use a gene encoding L-lactate dehydrogenase that converts pyruvic acid to L-lactic acid and, in cases where D-lactic acid is to be produced, it is preferred to use a gene encoding D-lactate dehydrogenase that converts pyruvic acid to D-lactic acid.

The lactate dehydrogenase gene is not limited as long as it is a gene capable of expressing lactate dehydrogenase that is active in yeast. Known examples of the lactate dehydrogenase gene capable of expressing lactate dehydrogenase that is highly active in yeast include an L-lactate dehydrogenase gene derived from *Xenopus laevis* (see JP 2008-29329 A and WO 2009/099044) and a D-lactate dehydrogenase gene derived from *Limulus polyphemus* (see WO 2010/140602). These genes can be preferably used for our mutants and in our methods.

In terms of the method of obtaining the lactic acid-producing yeast mutants from the lactic acid-producing yeast (hereinafter referred to as the parent strain), the lactic acid-producing yeast mutants can be preferably obtained by culturing the parent strain at the lactic acid fermentation optimum pH, or at a pH lower than the lactic acid fermentation optimum pH, of the parent strain, while inducing mutation in the parent strain, followed by culturing the resultant in a selection medium at a pH that is lower by not less than 0.5 than the lactic acid fermentation optimum pH supplemented with 0.5 to 10% (w/v) lactic acid. The term "lactic acid fermentation optimum pH" means the pH condition determined as follows. The parent strain is subjected to batch culture for a certain period at a pH of 4.0, 4.5, 5.0, 5.5 and 6.0, and the lactic acid concentration in each resulting medium is quantified to use it as the lactic acid productivity. The pH at which the lactic acid productivity was highest is regarded as the lactic acid fermentation optimum pH. In cases where the lactic acid productivity is highest at a plurality of pHs within a certain range, the lowest pH within the range is regarded as the lactic acid fermentation optimum pH. The lactic acid fermentation optimum pH of yeast depends on the species of the yeast used and, in cases where the lactic acid-producing yeast is *Saccharomyces cerevisiae*, the lactic acid fermentation optimum pH can be judged to be 4.5 according the result of Reference Example 2 in JP 2009-171879 A.

Examples of the method of inducing mutation in a yeast include: a method wherein mutation is randomly induced using ultraviolet, radiation or a mutation-inducing compound; a method that introduces spontaneous mutation that is obtained by acclimatization to acid using a chemostat; and site directed mutagenesis, which induces mutation to a specific genetic character(s). When the lactic acid-producing yeast mutants are to be obtained, they are preferably obtained by a method by randomly inducing mutation using a mutation-inducing agent. Examples of the method to induce mutation using a mutation-inducing agent to obtain a lactic acid-producing yeast mutant include methods in which a wild-type yeast is subjected to mutagenesis such as a method wherein a chemical mutagen N-methyl-N'-nitro-N-nitrosoguanidine (NTG) (Microbiology Laboratory Manual, 1986, p. 131, Kodansha Scientific), ethyl methanesulfonate (EMS), diethyl sulfate or 1-methyl-nitronitrosoguanidine (MNNG) is used (Methods in Yeast Genetics, 2002, pp. 9-17, Maruzen Co., Ltd.), and a method wherein a disparity mutagenesis plasmid (see Japanese Translated PCT Patent Application Laid-open No. 2006-521113) is used. In cases where the lactate dehydrogenase activity decreased in the process of preparation of a lactic acid-producing yeast mutant, the lactate dehydrogenase activity of the mutant can be recovered by re-introduction of the lactate dehydrogenase gene using the method disclosed in WO 2010/140602.

The medium composition of the medium upon the induction of mutation in the lactic acid-producing yeast is not limited and SD medium, which is a synthetic minimal medium, is preferably used. The medium composition of the selection medium to select a lactic acid-producing yeast mutant is not limited as long as a predetermined amount of lactic acid is contained therein and SD medium, which is a synthetic minimal medium, is preferably used. Further, the selection medium is preferably a solid medium with which colonies of lactic acid-producing yeast mutants can be selected.

The lactic acid contained in the selection medium for the lactic acid-producing yeast mutant is not limited and, in cases where an L-lactic acid-producing yeast mutant is to be selected, the lactic acid is preferably L-lactic acid and, in cases where a D-lactic acid-producing yeast mutant is to be selected, the lactic acid is preferably D-lactic acid. The optical purity of the L-lactic acid or D-lactic acid is preferably 90 to 99.9% e.e., more preferably 99 to 99.9% e.e.

Further, the lactic acid fermentation yeast mutants can also be obtained by inducing mutation in a yeast having no lactate dehydrogenase gene introduced therein, to obtain a low-pH resistant yeast, followed by introducing a lactate dehydrogenase gene to the obtained yeast. In terms of the method of obtaining the low-pH resistant yeast in this case, mutation may be induced by the above-described method in a yeast having no lactate dehydrogenase gene introduced therein.

Whether a yeast strain selected by the above method is our lactic acid-producing yeast mutant can be judged by comparing the lactic acid-producing ability of the mutant in a medium at pH 3 with the lactic acid-producing ability of the mutant or the parent strain at the lactic acid fermentation optimum pH based on the lactic acid concentration in the medium quantified, to confirm that the lactic acid-producing ability at pH 3 is equivalent to or higher than the lactic acid-producing ability at the lactic acid fermentation optimum pH. Further, even in cases where the lactic acid-producing ability of a mutant in a medium at pH 3 is compared to the lactic acid-producing ability of the mutant or the parent strain at the lactic acid fermentation optimum pH based on the lactic acid concentration in the medium quantified, to find that the lactic acid-producing ability in the medium at pH 3 is lower than the lactic acid-producing ability at the lactic acid fermentation optimum pH, if the decrease in the lactate dehydrogenase activity was caused by mutation of the lactate dehydrogenase gene, the lactic acid-producing yeast mutant can be obtained by recovering the damaged lactate dehydrogenase gene as described above. The reason why the lactic acid productivity in a medium at pH 3 is used as the criterion is that Reference Example 3 of JP 2009-171879 A discloses that batch culture of a lactic acid-producing yeast without alkali neutralization resulted in a pH of the medium of 2.8 so that the pH of the medium is assumed to stay at about 3 in cases where a lactic acid-producing yeast is subjected to batch culture without alkali neutralization. The medium used for comparison of the lactic acid-producing ability is not limited and SC medium, which is a synthetic complete medium, or a natural medium using raw sugar (see JP 2009-142210 A or JP 2009-171879 A) is preferably used.

Specific examples of the lactic acid-producing yeast mutants obtained by the above-described method include: mutants of the D-lactic acid-producing yeast described in WO 2010/140602 having a D-lactate dehydrogenase gene derived from *Limulus polyphemus* introduced therein, which are deposited under accession Nos. NITE BP-1087, NITE BP-1088 and NITE BP-1089; and mutants of the L-lactic acid-producing yeast described in WO 2009/099044 having an L-lactate dehydrogenase gene derived from *Limulus polyphemus* introduced therein, which are deposited with National Institute of Technology and Evaluation under accession Nos. NITE BP-1189 and NITE BP-1190.

The method of producing lactic acid using the lactic acid-producing yeast mutants (hereinafter referred to as the "mutant") is described below. The term "lactic acid" includes the free-form lactic acid, lactic acid salts and derivatives of lactic acid.

The medium to be used to culture the mutant may be either a natural medium or synthetic medium as long as it comprises a carbon source, nitrogen source, inorganic salts and/or the like that can be metabolized by the mutant, and it allows efficient culture of the yeast. Specific examples of the carbon source that may be used include: carbohydrates such as glucose, fructose, sucrose, galactose, maltose, raffinose, trehalose, sorbose, cellobiose, lactose, melibiose, melezitose, inulin, xylose, arabinose, ribose, rhamnose, glucosamine, erythritol, ribitol, mannitol, glucitol, salicin, starch and starch, and hydrolysates thereof; saccharified liquids obtained from cellulose and the like derived from biomass; organic acids such as acetic acid, propionic acid and citric acid; and alcohols such as ethanol and propanol. Specific examples of the nitrogen source that may be used include: ammonia; and ammonium salts of inorganic acids and organic acids such as ammonium chloride, ammonium sulfate, ammonium acetate and ammonium phosphate; other nitrogen-containing compounds; peptone; meat extracts; and corn steep liquors. Examples of the inorganic substance that may be used include potassium dihydrogenphosphate, magnesium phosphate, magnesium sulfate, sodium chloride, ferrous sulfate, manganese sulfate, copper sulfate and calcium carbonate. These carbon sources, nitrogen sources, inorganic salts and the like may be added at once upon the start of culture, or may be added separately or continuously during the culture.

The mutant may be usually cultured under conditions that achieve good lactic acid productivity, ranging from aerobic conditions in shaking culture, aeration/agitation culture and the like to anaerobic conditions without aeration. The culture temperature is not limited as long as the temperature condition allows the mutant to produce lactic acid, and the temperature is preferably 25 to 37° C., more preferably 28 to 35° C.

During culturing of the mutant, the pH of the culture liquid may be appropriately controlled, or the culture liquid may be buffered such that its pH is kept within a certain range, using an alkaline substance such as calcium hydroxide, calcium carbonate, sodium hydroxide, potassium hydroxide, aqueous ammonia or ammonia gas; an organic acid such as lactic acid, acetic acid, succinic acid, pyruvic acid, itaconic acid or citric acid; or a mineral acid such as hydrochloric acid or sulfuric acid. Since, as described later, gypsum may be generated in the subsequent step of separation/purification of lactic acid depending on the amount of alkaline substance added to the culture liquid, the pH of the culture liquid is preferably kept at not more than 3. To keep the pH of the culture liquid at a pH value of interest means that the pH of the culture liquid is controlled such that the pH value of interest is achieved, and the pH of the culture liquid may temporarily exceed the pH value of interest during the culture period as long as the culture step comprises such a control operation. Even in cases where the pH of the medium before the culture is higher than the pH value of interest, but the lactic acid produced by the culture decreases the pH of the culture liquid to below the pH value of interest, the operation is considered to be an operation that keeps the pH of the culture liquid at the pH value of interest.

The method of culturing the mutant is not limited as long as it allows fermentation production of the lactic acid of interest. Examples of the method that may be employed include batch culture, fed-batch culture, chemostat culture and continuous culture. Batch culture or the membrane-utilizing continuous culture described in WO 2007/097260 may be preferably employed.

The lactic acid contained in the culture liquid of the mutant may be separated/purified by a known method such as crystallization, extraction with an organic solvent, ion exchange, esterification distillation, or the separation/purification method disclosed in WO 2009/004922, wherein purification with a nanofiltration membrane is combined with distillation, or a combination of two or more of these. In cases where a lactic acid fermentation yeast is cultured at the lactic acid fermentation optimum pH, the lactic acid in the culture liquid is consequently present as a lactic acid salt because of alkali neutralization in the culture step. If free-form lactic acid is to be separated/purified from the culture liquid, the process of conversion of the lactic acid salt to the free form is required.

The process of conversion of the lactic acid salt to the free form requires an acid component such as sulfuric acid, and the process is accompanied by removal of by-products produced thereby such as gypsum. Utilization of properties of the mutant enables production of lactic acid while decreasing the amount of alkali added for the alkali neutralization in the step of culturing the mutant, or while keeping the pH of the culture liquid at not more than 3 by omitting the alkali neutralization. As a result, the process of conversion of a lactic acid salt to the free form in the step of separation/purification of free-form lactic acid can be omitted or simplified, and the method of producing lactic acid can therefore be preferably applied to cases of production of free-form lactic acid.

EXAMPLES

Our mutants and methods are described below more specifically by way of Examples, but this disclosure is not limited to the description of Examples.

Reference Example 1

Yeast Having D-lactate Dehydrogenase Gene Derived from *Limulus polyphemus* Introduced Therein As the parent strain to obtain our lactic acid-producing yeast mutant, the SU042 strain described in WO 2010/140602, which was prepared by introducing a D-lactate dehydrogenase gene derived from *Limulus polyphemus* into a yeast (*Saccharomyces cerevisiae*), was used.

Reference Example 2

Yeast Having L-lactate Dehydrogenase Gene Derived from *Xenopus laevis* Introduced Therein As the parent strain to obtain our lactic acid-producing yeast mutant, the HI003 strain described in WO 2009/099044, which was prepared by introducing an L-lactate dehydrogenase gene derived from *Xenopus laevis* into a yeast (*Saccharomyces cerevisiae*), was used.

Reference Example 3

Method for Analyzing Lactic Acid Concentration and Optical Purity by HPLC

The concentration of lactic acid was measured by HPLC under the following conditions:
  Column: Shim-Pack SPR-H (manufactured by Shimadzu Corporation)
  Mobile phase: 5 mM p-toluenesulfonic acid (flow rate, 0.8 mL/min.)
  Reaction solution: 5 mM p-toluenesulfonic acid, 20 mM Bis-Tris, 0.1 mM
  EDTA-2Na (flow rate, 0.8 mL/min.)
  Detection method: Electric conductivity
  Temperature: 45° C.

The optical purity of lactic acid was calculated according to the Equations below, based on the results of measurement of the L-lactic acid and D-lactic acid concentrations by HPLC under the following conditions:
  Column: TSK-gel Enantio L1 (manufactured by Tosoh Corporation)
  Mobile phase: 1 mM aqueous copper sulfate solution
  Flow rate: 1.0 ml/min.
  Detection method: UV 254 nm
  Temperature: 30° C.
  D-lactic acid optical purity (% e.e.)=$100 \times (D-L)/(L+D)$
  L-lactic acid optical purity (% e.e.)=$100 \times (L-D)/(L+D)$.
In these equations, L represents the concentration of L-lactic acid, and D represents the concentration of D-lactic acid.

Comparative Example 1

Evaluation of Lactic Acid-producing Ability of Lactic Acid-Producing Yeast

Figure 1:
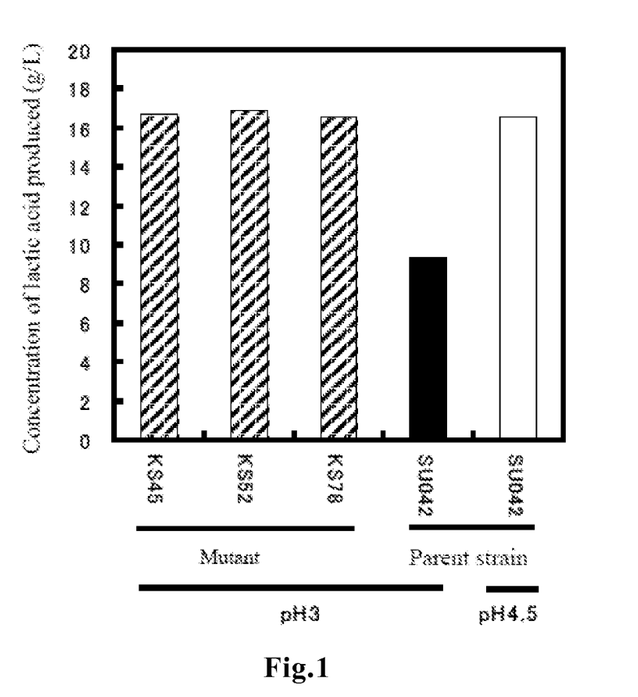
FIG. 1 is a diagram illustrating comparison of the D-lactic acid-producing ability between the SU042 strain, which is a D-lactic acid-producing parent yeast strain, and D-lactic acid-producing yeast mutants.

The SU042 strain described in Reference Example 1 was cultured with shaking at 30° C. for 72 hours in 5 ml of the medium prepared by adding D-lactic acid (>99.9 e.e.) to the fermentation medium of Table 1 at 2% (w/v) (pH 3; the pH was adjusted with calcium hydroxide) or in 5 ml of the fermentation medium of Table 1 whose pH was adjusted to the lactic acid fermentation optimum pH of *Saccharomyces cerevisiae* (the lactic acid fermentation optimum pH was judged to be 4.5 based on the lactic acid productivity of the lactic acid fermentation yeast described in Examples of JP 2009-171879 A) (pH 4.5). With the SU042 strain used as a parent strain of lactic acid-producing yeast mutants, the lactic acid-producing ability in the medium at pH 3 was compared to the lactic acid-producing ability at the lactic acid fermentation optimum pH (pH 4.5) based on the amount of lactic acid produced by the yeast. As a result, as shown in FIG. 1, it was confirmed that the lactic acid-producing ability in the medium at pH 3 was as low as about 55% of the lactic acid-productivity at the lactic acid fermentation optimum pH. The above results of evaluation of the lactic acid-producing ability were obtained by observing reproducible results three or more times.

TABLE 1

| Substance | Amount of component |
| --- | --- |
| Glucose | 50 g |
| Standard amino acids excluding leucine (19 types of amino acids) | 152 mg each |
| Leucine | 760 mg |
| Adenine | 436 mg |
| Uracil | 152 mg |
| Inositol | 78 mg |
| p-Aminobenzoic acid | 16.2 mg |
| Distilled water | 1000 ml |

(Adjusted to pH 4.5)

Example 1

Preparation of Lactic Acid-Producing Yeast Mutants and Evaluation of Their Lactic Acid-Producing Abilities The SU042 strain described in Reference Example 1 was subjected to mutation treatment with EMS (manufactured by Sigma-Aldrich). The SU042 strain was cultured for 24 hours in 2 ml of SD medium whose pH was adjusted to the lactic acid fermentation optimum pH (pH4.5) of *Saccharomyces cerevisiae*, and 0.5% of the resulting culture liquid was then inoculated to the same SD medium. The yeast was then cultured for 24 hours while EMS was added thereto to induce mutation in the lactic acid-producing yeast. Thereafter, 5% of the resulting culture liquid for induction of mutation was inoculated to 2 ml of SD medium supplemented with 2% (w/v) D-lactic acid (>99.9 e.e.) (pH 2.8; the pH was adjusted with calcium hydroxide), followed by 24 hours of culturing.

The culture liquid subjected to mutation treatment was further cultured for 72 hours in SD agar medium supplemented with 2% (w/v) D-lactic acid (>99.9 e.e.) whose pH was adjusted to 2.8 or 3.0 with calcium hydroxide, or in SD agar medium at pH 4.5, followed by selecting one strain from the agar medium at pH 2.8 (KS52), one strain (KS78) from the agar medium at pH 3.0 and one strain (KS45) from the SD agar medium at pH 4.5.

Each of the three selected strains was evaluated for its lactic acid-producing ability in 5 ml of the fermentation medium prepared by adding D-lactic acid (>99.9 e.e.) to the medium of Table 1 at 2% (w/v) (pH 3; the pH was adjusted with calcium hydroxide). The results of evaluation are shown in FIG. 1, together with the result obtained by culturing the parent strain at the lactic acid fermentation optimum pH (pH 4.5) for 72 hours. The lactic acid-producing ability of each selected strain was equivalent to or higher than the lactic acid-producing ability of the parent strain measured at the lactic acid fermentation optimum pH, and was confirmed to be about 1.8 times higher than the lactic acid-producing ability of the parent strain measured at pH 3. Based on these results, the selected three strains were determined to be lactic acid-producing yeast mutants that are resistant to a low pH state caused by lactic acid, and deposited with National Institute of Technology and Evaluation (the accession No. for the KS45 strain is NITE BP-1087; the accession No. for the KS52 strain is NITE BP-1088; and the accession No. for the KS78 strain is NITE BP-1089). The above results of evaluation of the lactic acid-producing ability were obtained by observing reproducible results three or more times.

Examples 2 to 4, Comparative Example 2

Evaluation of Lactic Acid-Producing Abilities of Lactic Acid-Producing Yeast Mutants in Batch Fermentation Each of the lactic acid-producing yeast mutants KS45 strain (Example 2), KS52 strain (Example 3) and KS78 strain (Example 4), and the parent strain SU042 strain (Comparative Example 2), was used for production of D-lactic acid by batch fermentation using the lactic acid fermentation medium shown in Table 2. As the raw sugar in the medium composition, "Okinawa no Yutosei" (manufactured by MUSO Co., Ltd.) was used, and the medium was autoclaved (121° C., 15 minutes) before use.

Evaluation of the lactic acid-producing ability was carried out under the following operating conditions:
Reaction vessel capacity (amount of lactic acid fermentation medium), 2 L (1 L); temperature control, 30° C.; reaction vessel aeration rate, 0.2 L/min.; reaction vessel stirring rate, 400 rpm; pH adjustment, carried out as appropriate with 5 N calcium hydroxide suspension.

Figure 2:
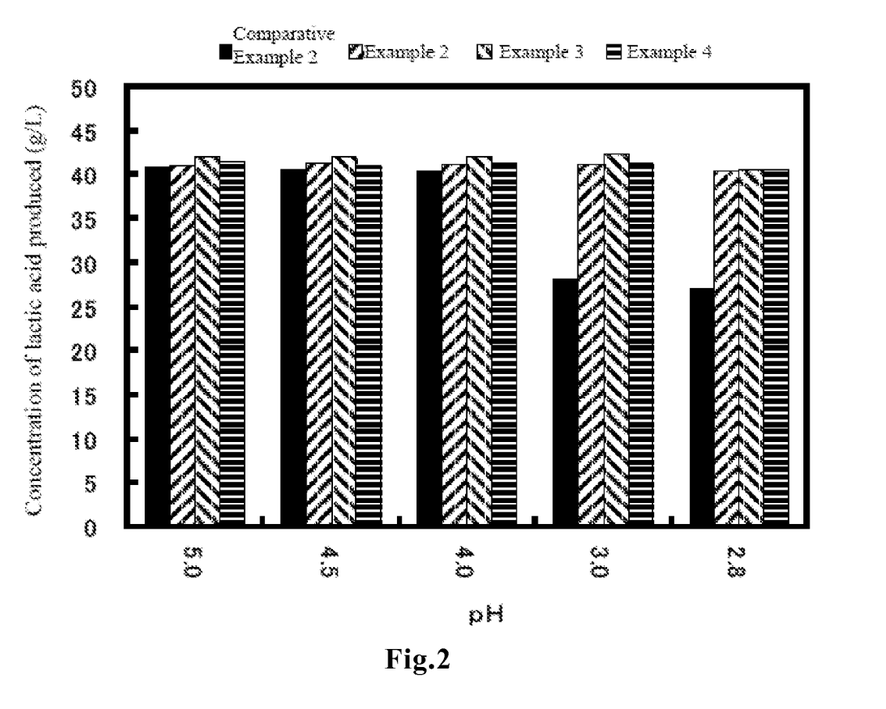
FIG. 2 is a diagram illustrating comparison of the lactic acid-producing ability at each pH between the SU042 strain, which is a D-lactic acid-producing parent yeast strain, and D-lactic acid-producing yeast mutants.

First, each of the three mutant strains was cultured with stirring overnight in 5 ml of the lactic acid fermentation medium of Table 1 placed in a test tube (pre-preculture). The obtained pre-preculture was inoculated to 50 ml of a fresh portion of the same fermentation medium as the medium used in the pre-preculturing, and cultured in a 500-ml Sakaguchi flask for 24 hours with shaking (preculture). The whole obtained preculture was inoculated to perform main culturing. The main culturing was carried out for 72 hours while the pH was adjusted to 5, 4.5, 4, 3 or 2.8. The result obtained by each batch culture is shown in FIG. 2. As a result, even at the pHs of as low as not more than 3, each of the three mutant strains showed a lactic acid-producing ability equivalent to or higher than that of the parent strain observed at the lactic acid fermentation optimum pH (pH4.5), and each mutant strain produced D-lactic acid with an optical purity of as high as not less than 99.9 e.e. On the other hand, the lactic acid-producing ability of the parent strain was much lower at the low pHs of not more than 3 than at the lactic acid fermentation optimum pH.

TABLE 2

| Substance | Amount of component |
|---|---|
| Raw sugar | 70 g |
| Ammonium sulfate | 1.5 g |
| Distilled water | 1000 ml |

Example 5, Comparative Example 3

Figure 3:
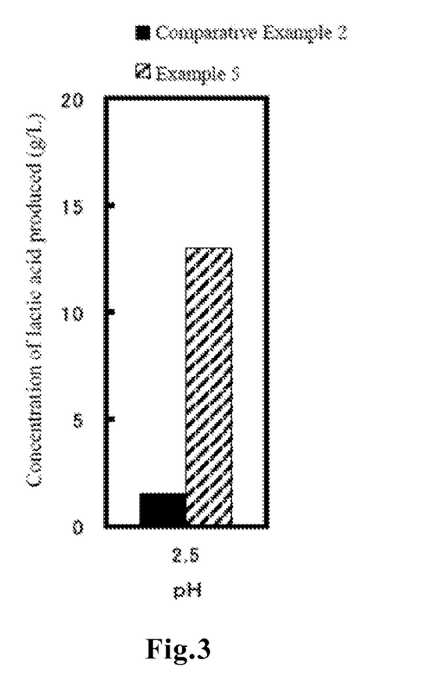
FIG. 3 is a diagram illustrating a comparison of the lactic acid-producing ability observed in culturing without alkali neutralization between the SU042 strain, which is a D-lactic acid-producing parent yeast strain, and a D-lactic acid-producing yeast mutant.

Evaluation of Lactic Acid-Producing Ability in Cases Where Lactic Acid-producing Yeast Mutant was Cultured without Alkali Neutralization Each of the lactic acid-producing yeast mutant KS78 (Example 5) and its parent strain, SU042 strain (Comparative Example 3), was inoculated to 5 ml of the lactic acid fermentation medium of Table 2 (pH 5), and cultured at 30° C. for 72 hours with shaking. The lactic acid-producing ability observed as a result is shown in FIG. 3. Although the pH of each culture liquid decreased to 2.5 by performing the culture without alkali neutralization, the mutant strain showed a lactic acid-producing ability about 9 times higher than that of the parent strain. Thus, it could be confirmed that use of our mutants allows highly efficient production of lactic acid without performing alkali neutralization in the culture step.

Comparative Example 4

Evaluation of Lactic Acid-Producing Ability of Lactic Acid-Producing Yeast

Figure 4:
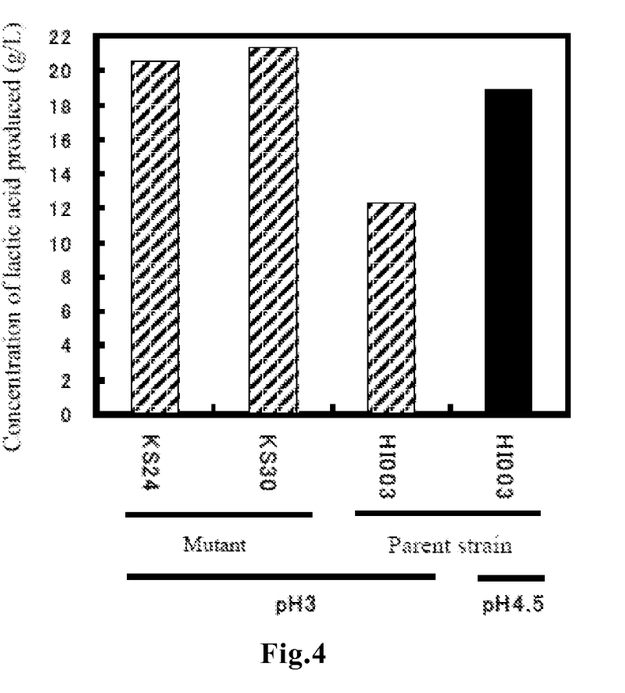
FIG. 4 is a diagram illustrating a comparison of the L-lactic acid-producing ability between the HI003 strain, which is an L-lactic acid-producing parent yeast strain, and L-lactic acid-producing yeast mutants.
Figure 5:
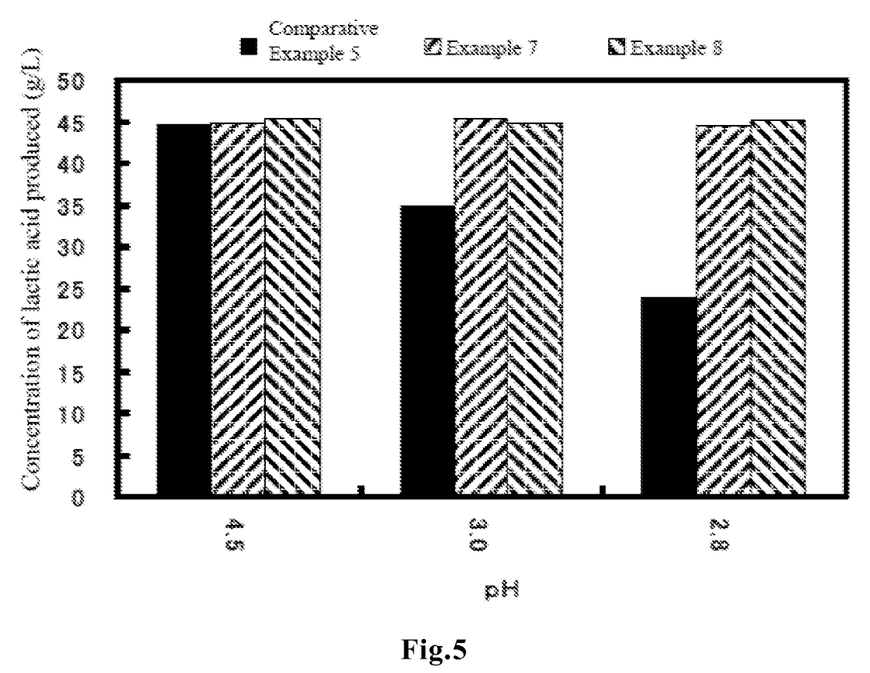
FIG. 5 is a diagram illustrating a comparison of the lactic acid-producing ability at each pH between the HI003 strain, which is an L-lactic acid-producing parent yeast strain, and L-lactic acid-producing yeast mutants.

The HI003 strain described in Reference Example 2 was cultured with shaking at 30° C. for 72 hours in 5 ml of the medium prepared by adding L-lactic acid (>99.9 e.e.) to the fermentation medium of Table 1 at 2% (w/v) (pH 3; the pH was adjusted with calcium hydroxide) or in 5 ml of the fermentation medium of Table 1 whose pH was adjusted to the lactic acid fermentation optimum pH of *Saccharomyces cerevisiae* (pH 4.5). With the HI003 strain used as the parent strain of lactic acid-producing yeast mutants, the lactic acid-producing ability in the medium at pH 3 was compared to the lactic acid-producing ability at the lactic acid fermentation optimum pH (pH 4.5) based on the amount of lactic acid produced by the yeast and, as a result, as shown in FIG. 4, it could be confirmed that the lactic acid-producing ability in the medium at pH 3 was as low as about 70% of the lactic acid-productivity at the lactic acid fermentation optimum pH. The above results of evaluation of the lactic acid-producing ability were obtained by observing reproducible results three or more times.

Example 6

Preparation of Lactic Acid-Producing Yeast Mutants and Evaluation of Their Lactic Acid-producing Abilities The HI003 strain described in Reference Example 2 was subjected to mutation treatment with EMS (manufactured by Sigma-Aldrich). The HI003 strain was cultured for 24 hours in 2 ml of SD medium whose pH was adjusted to the lactic acid fermentation optimum pH (pH4.5) of *Saccharomyces cerevisiae*, and 0.5% of the resulting culture liquid was then inoculated to the same SD medium. The yeast was then cultured for 24 hours while EMS was added thereto to induce mutation in the lactic acid-producing yeast. Thereafter, 5% of the resulting culture liquid for induction of mutation was inoculated to 2 ml of SD medium supplemented with 2% (w/v) L-lactic acid (>99.9 e.e.) (pH 2.8; the pH was adjusted with calcium hydroxide), followed by 24 hours of culturing.

The culture liquid subjected to mutation treatment was further cultured for 72 hours in SD agar medium supplemented with 2% (w/v) L-lactic acid (>99.9 e.e.) whose pH was adjusted to 2.8 with calcium hydroxide, or in SD agar medium at pH 4.5, followed by selecting one strain from the agar medium at pH 2.8 (KS24) and one strain (KS30) from the SD agar medium at pH 4.5.

Each of the two selected strains was evaluated for its lactic acid-producing ability in 5 ml of the fermentation medium prepared by adding L-lactic acid (>99.9 e.e.) to the medium of Table 1 at 2% (w/v) (pH 3; the pH was adjusted with calcium hydroxide). The results of evaluation are shown in FIG. 4, together with the result obtained by culturing the parent strain at the lactic acid fermentation optimum pH (pH4.5) for 72 hours. The lactic acid-producing ability of each selected strain was equivalent to or higher than the lactic acid-producing ability of the parent strain measured at the lactic acid fermentation optimum pH, and was confirmed to be about 1.7 times higher than the lactic acid-producing ability of the parent strain measured at pH 3. Based on these results, the selected two strains were judged to be lactic acid-producing yeast mutants that are resistant to a low pH state caused by lactic acid, and deposited with National Institute of Technology and Evaluation (the accession No. for the KS24 strain is NITE BP-1189; and the accession No. for the KS30 strain is NITE BP-1190). The above results of evaluation of the lactic acid-producing ability were obtained by observing reproducible results three or more times.

Examples 7 to 8, Comparative Example 5

Evaluation of Lactic Acid-Producing Abilities of Lactic Acid-Producing Yeast Mutants in Batch Fermentation Each of the lactic acid-producing yeast mutants KS24 strain (Example 7) and KS30 strain (Example 8), and the parent strain HI003 strain (Comparative Example 5), was used for production of L-lactic acid by batch fermentation using the lactic acid fermentation medium shown in Table 2. The medium, culture conditions and the like were the same as those in Examples 2 to 4 and Comparative Example 2 described above. As a result, even at the pHs of as low as not more than 3, each of the two mutant strains showed a lactic acid-producing ability equivalent to or higher than that of the parent strain observed at the lactic acid fermentation optimum pH (pH4.5), and each mutant strain produced L-lactic acid with an optical purity of as high as not less than 99.9 e.e. On the other hand, the lactic acid-producing ability of the parent strain was much lower at the low pHs of not more than 3 than at the lactic acid fermentation optimum pH.

Example 9, Comparative Example 6

Figure 6:
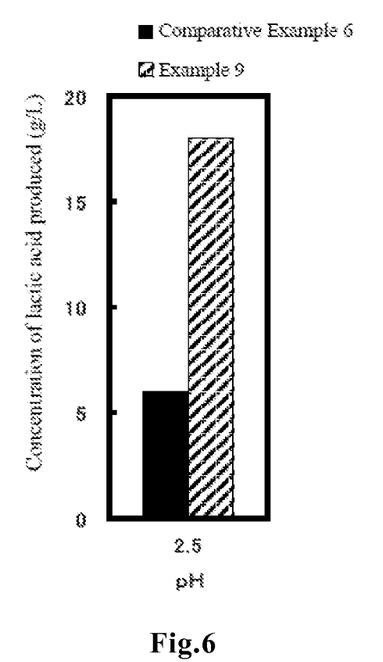
FIG. 6 is a diagram illustrating a comparison of the lactic acid-producing ability observed in culturing without alkali neutralization between the HI003 strain, which is an L-lactic acid-producing parent yeast strain, and an L-lactic acid-producing yeast mutant.

Evaluation of Lactic Acid-Producing Ability in Cases Where Lactic Acid-Producing Yeast Mutant was Cultured without Alkali Neutralization Each of the lactic acid-producing yeast mutant KS24 strain (Example 7) and its parent strain, HI003 strain (Comparative Example 5), was inoculated to 5 ml of the lactic acid fermentation medium of Table 2 (pH 5), and cultured at 30° C. for 72 hours with shaking. The lactic acid-producing ability observed as a result is shown in FIG. 6. Although the pH of each culture liquid decreased to 2.5 by performing the culture without alkali neutralization, the mutant strain showed a lactic acid-producing ability about 3 times higher than that of the parent strain. Thus, it could be confirmed that use of our mutants allows highly efficient production of lactic acid without performing alkali neutralization in the culture step.

INDUSTRIAL APPLICABILITY

Our lactic acid-producing yeast mutants can be used for foods and pharmaceuticals, and can be used for production of lactic acid as a raw material for biodegradable polymers.
Accession Numbers
NITE BP-1087 (Name of depositary: Patent Microorganisms Depositary, National Institute of Technology and Evaluation (NPMD); Address of depositary: 2-5-8 Kazusakamatari, Kisarazu-shi, Chiba 292-0818 Japan; Date of deposition: Apr. 25, 2011)
NITE BP-1088 (Name of depositary: Patent Microorganisms Depositary, National Institute of Technology and Evaluation (NPMD); Address of depositary: 2-5-8 Kazusakamatari, Kisarazu-shi, Chiba 292-0818 Japan; Date of deposition: Apr. 25, 2011)
NITE BP-1089 (Name of depositary: Patent Microorganisms Depositary, National Institute of Technology and Evaluation (NPMD); Address of depositary: 2-5-8 Kazusakamatari, Kisarazu-shi, Chiba 292-0818 Japan; Date of deposition: Apr. 25, 2011)
NITE BP-1189 (Name of depositary: Patent Microorganisms Depositary, National Institute of Technology and Evaluation (NPMD); Address of depositary: 2-5-8 Kazusakamatari, Kisarazu-shi, Chiba 292-0818 Japan; Date of deposition: Dec. 22, 2011)
NITE BP-1190 (Name of depositary: Patent Microorganisms Depositary, National Institute of Technology and Evaluation (NPMD); Address of depositary: 2-5-8 Kazusakamatari, Kisarazu-shi, Chiba 292-0818 Japan; Date of deposition: Dec. 22, 2011)

The invention claimed is:

1. A lactic acid-producing yeast mutant which is a mutant of a yeast prepared by introduction of a lactate dehydrogenase gene that results in lactic acid-producing ability, said mutant having, in a medium at pH 3, a lactic acid-producing ability equivalent to or higher than the lactic acid-producing ability of a parent strain of said mutant at a lactic acid fermentation optimum pH, wherein said lactate dehydrogenase gene is a gene encoding D-lactate dehydrogenase or a gene encoding L-lactate dehydrogenase and,
  when the lactate dehydrogenase gene is a gene encoding D-lactate dehydrogenase, said gene encoding D-lactate dehydrogenase is derived from *Limulus polyphemus*, and
  when the lactate dehydrogenase gene is a gene encoding L-lactate dehydrogenase, said gene encoding L-lactate dehydrogenase is derived from *Xenopus laevis*.

2. The lactic acid-producing yeast mutant according to claim 1, wherein said yeast belongs to the genus *Saccharomyces*.

3. The lactic acid-producing yeast mutant according to claim 1, wherein said yeast is *Saccharomyces cerevisiae*.

4. A method of producing lactic acid comprising culturing the lactic acid-producing yeast mutant according to claim 1.

5. The method according to claim 4, further comprising maintaining the culture liquid of said lactic acid-producing yeast mutant at a pH of not more than 3.

6. The method for producing lactic acid according to claim 4, further comprising culturing said lactic acid-producing yeast mutant without alkali neutralization of the culture liquid.

7. The lactic acid-producing yeast mutant according to claim 2, wherein said yeast is *Saccharomyces cerevisiae*.

* * * * *